United States Patent
Löwgren et al.

(10) Patent No.: US 12,005,267 B2
(45) Date of Patent: Jun. 11, 2024

(54) ILLUMINATION APPARATUS

(71) Applicant: BRAINLIT AB, Lund (SE)

(72) Inventors: Truls Olof Johan Löwgren, Malmö (SE); Peter K Andersson, Skäret (SE); Tord Wingren, Lund (SE)

(73) Assignee: BRAINLIT AB, Lund (SE)

( * ) Notice: Subject to any disclaimer, the term of this patent is extended or adjusted under 35 U.S.C. 154(b) by 0 days.

(21) Appl. No.: 18/178,577

(22) Filed: Mar. 6, 2023

(65) Prior Publication Data
US 2023/0201623 A1   Jun. 29, 2023

Related U.S. Application Data

(63) Continuation of application No. 16/642,427, filed as application No. PCT/EP2018/073017 on Aug. 27, 2018, now Pat. No. 11,596,804.

(30) Foreign Application Priority Data

Aug. 28, 2017 (EP) .................... 17188135

(51) Int. Cl.
*A61N 5/06* (2006.01)
(52) U.S. Cl.
CPC .......... *A61N 5/0618* (2013.01); *A61N 5/0625* (2013.01); *A61N 2005/0663* (2013.01)
(58) Field of Classification Search
CPC .............. A61N 5/0618; A61N 5/0625; A61N 2005/0663; A61N 2005/0658; Y02B 20/40; A61M 21/00; A61M 2021/0044
See application file for complete search history.

(56) References Cited

U.S. PATENT DOCUMENTS

| | | |
|---|---|---|
| 9,560,714 B1 | 1/2017 | Hjerde |
| 2010/0060195 A1 | 3/2010 | Tsuboi et al. |
| | (Continued) | |

FOREIGN PATENT DOCUMENTS

| | | |
|---|---|---|
| CN | 101589652 A | 11/2009 |
| CN | 102986299 A | 3/2013 |
| | (Continued) | |

OTHER PUBLICATIONS

International Search Report from International Application No. PCT/EP2018/073017, dated Nov. 29, 2018.
Extended European Search Report (ESSR) dated Feb. 1, 2018.

*Primary Examiner* — Brian T Gedeon
*Assistant Examiner* — Joshua Andrew Schum-Houck
(74) *Attorney, Agent, or Firm* — Shih IP Law Group, PLLC

(57) ABSTRACT

An illumination apparatus is disclosed, comprising: a first light source having a first spectral light distribution with a first light intensity peak about a first peak wavelength, and a second light source having a second spectral light distribution with a second light intensity peak about a second peak wavelength being different from the first peak wavelength, a third light source having a third spectral light distribution with a main light intensity peak about a third peak wavelength being different from the first peak wavelength and from the second peak wavelength, wherein the illumination apparatus is configured to provide adjustment of light intensity of the first light source and of light of the second light source, wherein the illumination apparatus provides an adjustment of light intensity of the third light source to compensate for the adjusting of the relative light intensity between the first light source and the second light source.

11 Claims, 4 Drawing Sheets

(56) References Cited

U.S. PATENT DOCUMENTS

| | | |
|---|---|---|
| 2010/0063566 A1 | 3/2010 | Uchiumi et al. |
| 2010/0174345 A1* | 7/2010 | Ashdown ............... H05B 45/22 |
| | | 607/88 |
| 2014/0052220 A1* | 2/2014 | Pedersen ............... A61M 21/00 |
| | | 607/88 |
| 2014/0228914 A1 | 8/2014 | van de Ven et al. |
| 2014/0248678 A1 | 9/2014 | Nigola et al. |
| 2016/0016001 A1* | 1/2016 | Loupis ................... H05B 45/20 |
| | | 604/20 |

FOREIGN PATENT DOCUMENTS

| | | |
|---|---|---|
| EP | 2094064 A1 | 8/2009 |
| EP | 2199657 A2 | 6/2010 |
| WO | 2008052318 A1 | 5/2008 |
| WO | 2012011008 A | 1/2012 |
| WO | 2015052207 A1 | 4/2015 |

* cited by examiner

ILLUMINATION APPARATUS

CROSS-REFERENCE

This application is a Continuation of U.S. application Ser. No. 16/642,427, filed Feb. 27, 2020; which is a National Stage Entry of PCT/EP2018/073017, filed Aug. 27, 2018; which claims the benefit of European Application No.: 17188135.2, filed Aug. 28, 2017.

TECHNICAL FIELD

The present invention relates to an illumination apparatus.

BACKGROUND OF THE INVENTION

Light plays a fundamental role for the well-being of humans. In nature, the natural light varies in color spectra and intensity during the day. In the morning, the daylight has a bluer tone stimulating alertness. In the evening, the natural light turns redder which improves relaxation. More specifically, it is known that the bluer light in the morning increases cortisol and reduces melatonin increasing attentiveness and focus, while the warmer red tone increases the body's melatonin and reduces cortisol causing the relaxation.

There is therefore an interest in mimicking natural light for achieving improvements in well-being and productivity. Recent advances in LED-based lighting technologies allows for the desired mimicking of natural light in indoor environments. The illumination at the workplace should, however, be adapted to the work to be performed and it should also be adapted to the needs of each individual. Thus, there is a desire for more flexible illumination sources for indoor environments.

SUMMARY OF THE INVENTION

In view of the above, it is an object of the present invention to provide an illumination apparatus allowing for improved tailoring of the spectral light distribution of the light emitted.

According to a first aspect an illumination apparatus is provided. The illumination apparatus comprising:

a first light source configured to emit light having a first spectral light distribution having a first main light intensity peak about a first peak wavelength providing light stimulation, wherein the first light source is a cold white light emitter and the first peak wavelength is within the range of 450-490 nm, a second light source configured to emit light having a second spectral light distribution having a second main light intensity peak about a second peak wavelength being different from the first peak wavelength, wherein the second light source is a cold white light emitter and the second peak wavelength is within the range of 440-450 nm or 490-500 nm, and wherein the first and second peak wavelengths are close in wavelength, within 10% of the visible spectral wavelength range, and a third light source configured to emit light having a third spectral light distribution having a third main light intensity peak about a third peak wavelength being different from the first peak wavelength and from the second peak wavelength, wherein the third light source is a warm white light emitter and the third peak wavelength is within the range of 500-700 nm, wherein the illumination apparatus is configured to provide adjustment of light intensity of the first light source and of the second light source, thereby providing a relative light intensity between the first light source and the second light source, wherein the illumination apparatus is configured to provide adjustment of light intensity of the third light source in to order to compensate for the adjusting of the relative light intensity between the first light source and the second light source.

An improved tailoring of the spectral light distribution from the illumination apparatus is thereby provided. The tuning of the light intensity of the first light source relative to the light intensity of the second light source and compensation of light intensity of the third light source allows for a substantially maintained overall light output from the illumination apparatus. A reduced perceived change of the light emitted by the illumination apparatus is thereby obtained although there is a change in the relative light intensity between the first light source and the second light source.

The light emitted by the first light source may have a stimulating effect whereas the light emitted by the second light source may have a non-stimulating effect. The illumination apparatus thereby allows for efficient transitions between stimulation and non-stimulation while keeping a substantially unchanged spectral light distribution as perceived by a user illuminated by the illumination apparatus.

The wording light stimulation may be construed as light suitable for inducing a biological and/or behavioral effect on a human or animal. The biological and/or behavioral effects may include a change in melatonin secretion, body temperature, cortisol secretion, heart rate, alertness, cognitive performance, psychomotor performance, brain blood flow and/ or EEG response.

The first peak wavelength may be within the range of 450-512 nm, preferably 450-490 nm.

The first light source may be a cold white light emitter and the first peak wavelength is within the range of 450-512 nm.

The light emitted by the first light source may thereby have a stimulating effect as the sensitivity of the melanopsin receptors is reported to be in the span of 450-520 nm, typically having a peak sensitivity in the range 470-490 nm. The light emitted by the first light source may thereby increases cortisol and suppress melatonin in humans whereby an increasing attentiveness and focus may be achieved for a user illuminated by the illumination apparatus.

The second peak wavelength may be within the range of 440-450 nm or 490-500 nm.

When the second peak wavelength is within the range of 440-450 nm the second peak wavelength is preferably at least 7 nm smaller than the first peak wavelength.

When the second peak wavelength is within the range of 490-500 nm the second peak wavelength is preferably at least 7 nm larger than the first peak wavelength.

Such a difference in peak wavelengths is considered suitable for providing a possibility to balance stimulating effect and perceived relative light intensity.

The second peak wavelength ranges are near but outside the wavelength range of the first peak wavelength, i.e. 450-490 nm. A lower suppression of melatonin may thereby be achieved by the light having the second peak wavelength. The light emitted by the second light source may thereby have a less stimulating effect.

The second light source may have a 50% intensity over a spectral wavelength range of at least 70 nm.

The third light source may be a green light emitter and the third peak wavelength is within the range of 490-580 nm.

The third light source may be a red light emitter and the third peak wavelength is within the range of 630-700 nm.

The illumination apparatus may further comprise a fourth light source configured to emit light having a fourth spectral light distribution having a fourth main light intensity about a fourth peak wavelength being different from the first peak wavelength, from the second peak wavelength and from the third peak wavelength, wherein the illumination apparatus is configured to provide adjustment of light intensity of the fourth light source in to order to in combination with the adjusting of the third light source compensate for the adjusting of the relative light intensity between the first light source and the second light source.

An improved tailoring of the overall spectral light distribution of the light emitted by the illumination apparatus is thereby achieved. A desired color balance of the light may thereby be achieved with greater accuracy.

The fourth light source may be a red light emitter and the fourth peak wavelength is within the range of 630-700 nm.

The illumination apparatus may further comprise a further light source configured to emit light having a further spectral light distribution having a further main light intensity peak about a further peak wavelength being different from the first peak wavelength and from the second peak wavelength, the further peak wavelength being chosen to enhance the light stimulation provided by the first light source.

The apparatus may be configured to provide adjustment of light intensity of the further light source.

The further light may have a main light intensity peak at a peak wavelength within the range of 580-630 nm.

The further light source allows for light exposure at longer wavelength light, i.e. 580-630 nm in the orange-red part of the visible spectrum. Light within the range of 580-630 nm may trigger melanopsin chromophore regeneration and an increased subsequent intrinsic photosensitivity of intrinsically photosensitive retinal ganglion cells, ipRGCs. An improved suppression of melanin may thereby be obtained.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

FIG. 3b illustrates another spectral distribution of light emitted by the same illumination apparatus as in FIG. 3a.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

Figure 1:
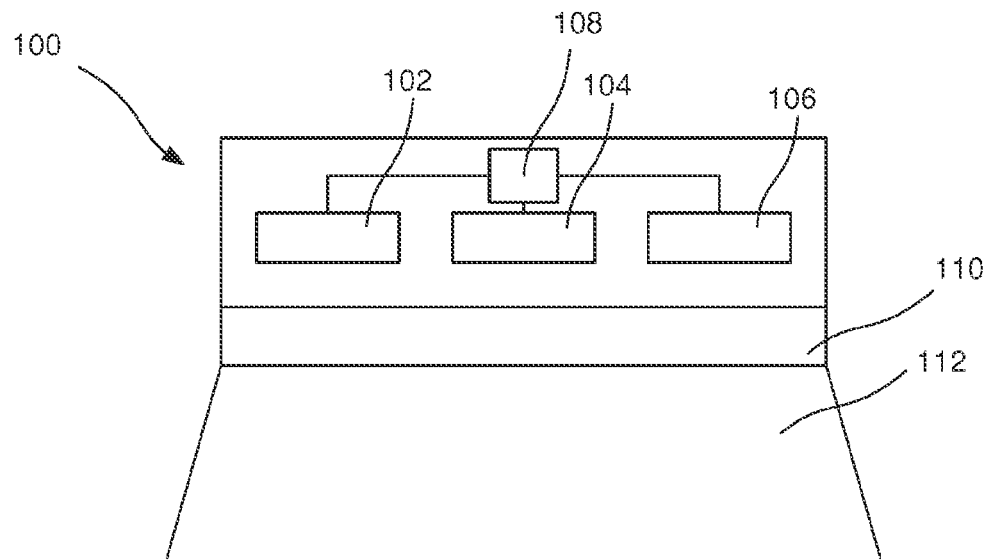
FIG. 1 illustrates an illumination apparatus.

FIG. 1 illustrates an illumination apparatus 100. The illumination apparatus 100 comprises a first light source 102, a second light source 104 and a third light source 106. The illumination apparatus 100 may further comprise circuitry 108 for controlling the respective light sources 102, 104 and 106. The illumination apparatus 100 may comprise a light diffusing element 110 arranged to mix and diffuse the light emitted by the respective light source 102, 104, and 106. Light may thereby be emitted with improved spatial uniformity. A more uniform distribution of the spectral distribution of the light emitted 112 by the illumination apparatus 100 may also be obtained. The light diffusing element 110 may mix of the light emitted by the respective light source 102, 104, and 106, by scattering and/or multiple reflection within the light diffusing element 110.

Figure 2A:
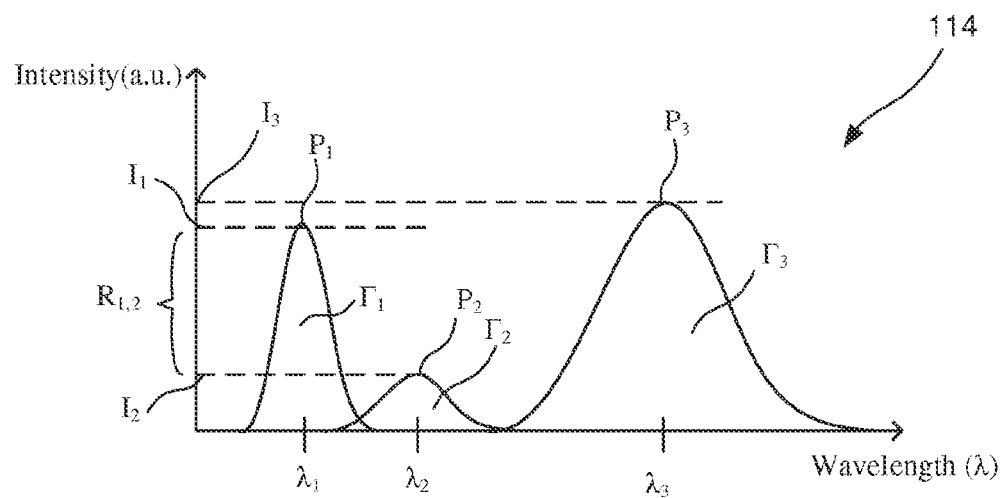
FIG. 2a illustrates a spectral distribution of light emitted by an illumination apparatus at a first situation.

The first light source 102 is configured to emit light having a first spectral light distribution $\Gamma_1$, with a first main light intensity peak $P_1$, about a first peak wavelength $\lambda_1$, see FIG. 2a. The first light source 102 is further configured to emit light providing light stimulation, as will be discussed below.

The second light source 104 is configured to emit light having a second spectral light distribution $\Gamma_2$, with a second main light intensity peak $P_2$, about a second peak wavelength $\lambda_2$. The second peak wavelength $\lambda_2$ is different from the first peak wavelength $\lambda_2$.

The third light source 106 is configured to emit light having a third spectral light distribution $\Gamma_3$ having a third main light intensity peak $P_3$ about a third peak wavelength $\lambda_3$. The third peak wavelength $\lambda_3$ is different from the first peak wavelength and from the second peak wavelength, see FIG. 2a. The first light distribution $\Gamma_1$ and the second light distribution $\Gamma_2$ are in FIG. 2a illustrated to be overlapping, but may alternatively cover wavelength ranges which are not overlapping. To this end, the first $\lambda_1$ and the second $\lambda_2$ peak wavelengths may, be close in wavelength, within 10% of the visible spectral wavelength range.

The illumination apparatus 100 is configured to provide adjustment of light intensity of the first light source 102 and of the second light source 104, thereby providing a relative light intensity $R_{1,2}$ between the first light source 102 and the second light source 104. To illustrate this, FIG. 2a shows the spectral distribution of light emitted by the illumination apparatus 100 at a first situation 114 in which the relative intensity $R_{1,2}$ is set such that the light intensity $I_1$ of the light emitted by the first light source 102 is larger than the light intensity $I_2$ of the light emitted by the second light source 104.

Figure 2B:
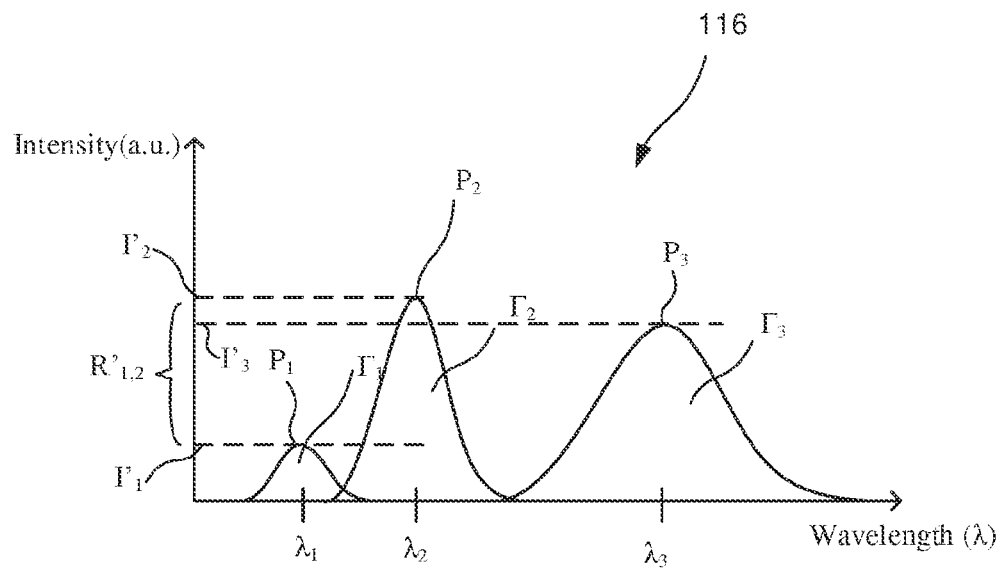
FIG. 2b illustrates a spectral distribution of light emitted by the same illumination apparatus as in FIG. 2a at a second situation.

As a comparison, FIG. 2b illustrates a spectral distribution of light emitted by the same illumination apparatus 100 at a second situation 116. In the second situation 116 the light intensity of the light emitted by the first light source 102 and the second light source 104 is adjusted relative to the first situation 114. As a non-limiting example, a relative intensity $R'_{1,2}$ is achieved such that the light intensity $I'_2$ of the light emitted by the second light source 104 is larger than the light intensity of the light emitted by the first light source 102.

The spectral light distribution of the light emitted 112 by the illumination source 100 may thereby be set to a desired value. As the light emitted by the first light source 102 may have a stimulating effect, whereas the light emitted by the second light source 104 may have a non-stimulating effect the degree of stimulation may be set to a desired value by adjusting the relative light intensity $R_{1,2}$ to a desired value.

It may be noted, that the relative ratio of the relative light ratio may be understood to be any value. The relative intensity may further include zero or infinite, if there is no light or substantially no light emitted by one of the first light source 102 or the second light source 104 relative to the other light source.

The illumination apparatus 100 is further configured to provide adjustment of light intensity of the third light source 106 to compensate for the adjusting of the relative light intensity $R_{1,2}$ between the first light source 102 and the second light source 104 the illumination apparatus 100. The illumination apparatus 100 thereby allows for a tuning of the relative light intensity $R_{1,2}$ while keeping a substantially unchanged spectral light distribution of the light emitted 112 by the illumination apparatus 100. Again, referring to FIGS. 2a and 2b, this is illustrated by the varied light intensity of the third light source 106, compare $I_3$ to $I'_3$.

Figure 3A:
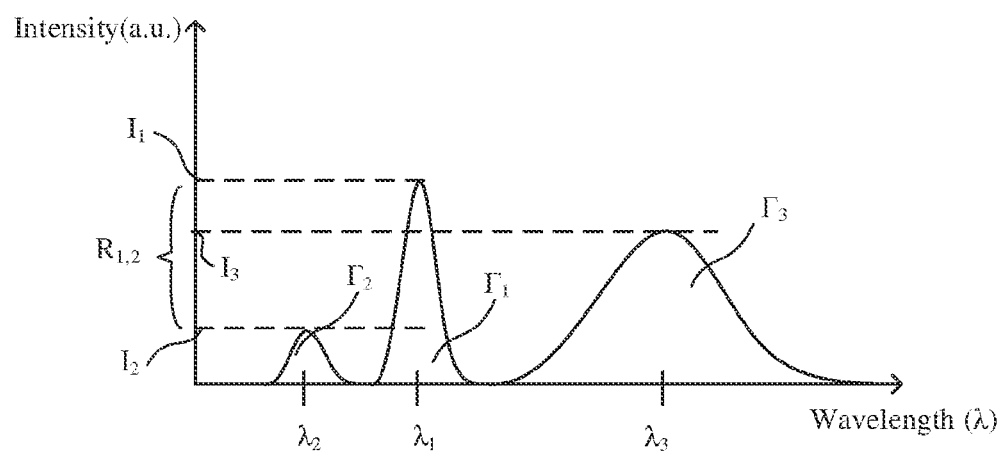
FIG. 3a illustrates a spectral distribution of light emitted by an illumination apparatus.
Figure 3B:
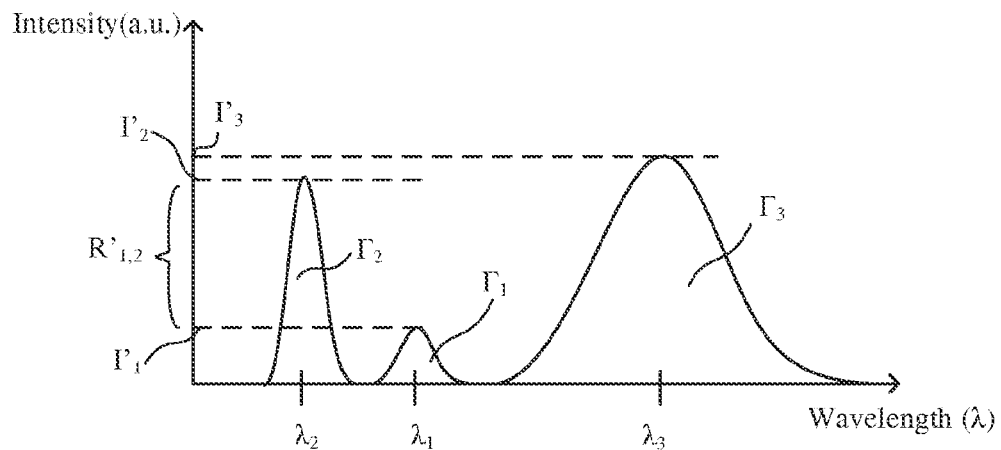

In the following, an example of light stimulation achievable by the illumination apparatus 100 is discussed, with reference to FIGS. 3a and 3b.

It is known that the sensitivity of melanopsin receptors appear to be in the wavelength range 450-490 nm, commonly reported to be in the range 450-520 nm, typically having a peak sensitivity in the range 470-490 nm. Thus, light emitted in the wavelength range 450-490 nm influences, for example, hormone secretion, heart rate, body temperature, sleep propensity and/or alertness for humans. Also animals are affected by light in the above wavelength range. To this end, melanopsin photoreceptors are sensitive to a range of wavelengths and have a peak light absorption at blue light wavelengths around 480 nm. It may be noted that other wavelengths of light activate the melanopsin signaling system with decreasing efficiency as they move away from the optimum 480 nm.

Thus, the light emitted by the first light source 102 may have a stimulating effect by increasing cortisol and suppression of the production of melatonin in humans. As a result, an increased attentiveness and focus may be achieved for a user illuminated by the illumination apparatus.

To achieve the above stimulation, the first peak wavelength $\Gamma_1$ may be selected to be within the range of 450-512 nm, preferably 450-490 nm.

Thus, the first light source may be arranged to emit light having a first spectral light distribution having a first main light intensity peak about a first peak wavelength within the range of 450-512 nm, preferably 450-490 nm.

The first peak wavelength $\lambda_1$ may be selected within the range of 460-490 nm.

The first peak wavelength $\lambda_1$ may be selected within a wavelength range comprising wavelengths larger than 450 nm.

The first peak wavelength $\lambda_1$ may be selected within a wavelength range comprising wavelengths smaller than 512 nm, preferably below 490 nm.

The first peak wavelength $\lambda_1$ may be selected within the range of 470-490 nm.

The first peak wavelength $\lambda_1$ may be selected to be at 480 nm.

The first light source 102 may, for instance, emit blue light at 460 nm. The first light source 102 may be a light emitting diode or a laser diode.

To provide an alternative light source, e.g. in the blue wavelength range of visible light, commonly defined to be in the range 400 to 500 nm, see e.g. Edwin R. Jones. Physics 153 Class Notes. University of South Carolina, 1999, the second peak wavelength $\lambda_2$ may be within the range of 440-450 nm or 490-500 nm. Light within this wavelength ranged have a lower stimulating effect than the light emitted having a first spectral light distribution having a first main light intensity peak about the first peak wavelength at 450-490, e.g. at 460 nm.

The skilled person is knowledgeable of that different definitions of which wavelength range that corresponds to a give color exists. Blue color may for example alternatively be defined to be within the wavelength range 424-491 nm, see e.g. CRC Handbook of Chemistry and Physics, 1966.

The second light source 104 may, for instance, emit blue light at 440-450 nm, also referred to as "Royal blue". The first light source 102 may be a light emitting diode or a laser diode. As discussed, in relation to FIGS. 2a and 2b above, the illumination apparatus 100 is configured to provide adjustment of light intensity of the first light source 102 and of the second light source 104, thereby providing a relative light intensity $R_{1,2}$ between the first light source 102 and the second light source 104. Thus, the relative light intensity $R_{1,2}$ determines the degree of stimulation of the light emitted 112 by the illumination apparatus 100. More specifically, the light emitted 112 by the illumination apparatus 100 in FIG. 3a has a stimulating effect as the light intensity $I_1$ of the light emitted by the first light source 102 is larger than the light intensity $I_2$ emitted by the second light source 104. In contrast, in FIG. 3b, the relative light intensity is changed to $R'_{1,2}$, for which the light intensity $I'_2$ of the light emitted by the second light source 104 is larger than the light intensity of the light emitted by the first light source 102. Thus the light emitted 112 in FIG. 3b has a lower or no stimulating effect.

Alternatively, the first peak wavelength $\lambda_1$ may be selected to be within the range of 470-490 nm. The second peak wavelength $\lambda_2$ may then be selected to be within the range of 450-470 nm or 490-500 nm. The first and the second peak wavelength may differ by at least 5 nm, preferably 7 nm. The illumination apparatus 100 is further configured to provide adjustment of light intensity $I_3$ of the third light source 106 to compensate for the adjusting of the relative light intensity $R_{1,2}$ between the first light source 102 and the second light source 104 the illumination apparatus 100, illustrated by the varied light intensity of the third light source 106, compare $I_3$ to $I'_3$ in FIGS. 3a and 3b, respectively. $I'_3$ is thereby larger than $I_3$. The illumination apparatus 100 thereby allows for a tuning of the relative light intensity, $R_{1,2}$ versus $R'_{1,2}$, while keeping a substantially unchanged spectral light distribution of the light emitted 112 by the illumination apparatus 100. A reduced perceived change in the overall light distribution of the light emitted 112 is thereby achieved.

The third light source 106 may be a light emitting diode emitting white light. The white light may be generated by the use of phosphors together with a short-wavelength LED, e.g. a phosphor material emitting light with a broad spectral light distribution, typically 500-700 nm, which is illuminated by blue light around 450 to 470 nanometers.

Figure 4:
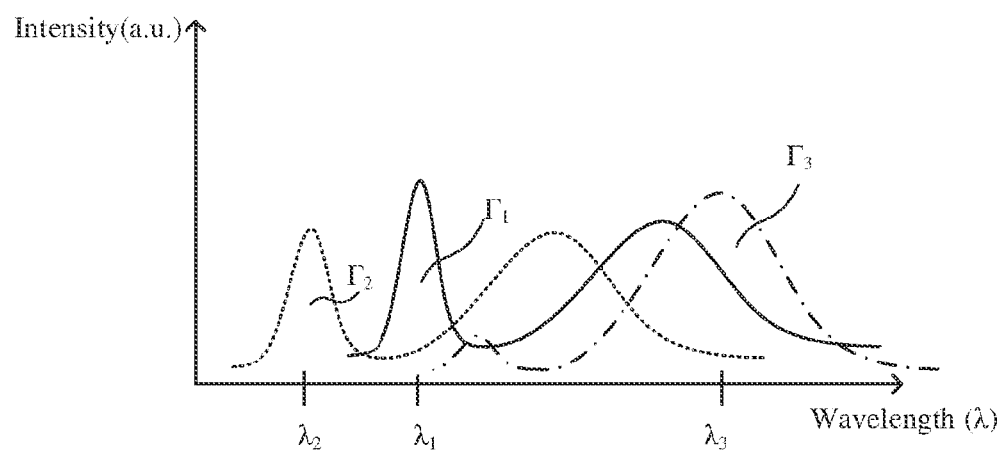
FIG. 4 illustrates a spectral distribution of light emitted by an illumination apparatus.

The first light source 102 may alternatively be a cold white light emitter, see solid line in FIG. 4, and the first peak wavelength may be within the range of 450-490 nm as discussed above.

The second light source 104 may be a cold white light emitter and the second peak wavelength is within the range of 440-450 nm, see the dashed line in FIG. 4. Thus, the relative intensity of the light emitted by the respective cold white light emitters may be used to tailor the stimulating effect of the light emitted by the illumination apparatus.

The second light source 104 may alternatively be a cold white light emitter and the second peak wavelength is within the range of 490-500 nm.

A cold white light emitter may be defied as a light source producing white light having a color temperature of 5000-9500 K CCT, where the Color Correlated Temperature, CCT, of light is defined as the temperature of the Planckian radiator whose perceived color most closely resembles that of a given stimulus at the same brightness and under specified viewing conditions. The skilled person realizes that other color temperature ranges may be used to define the color of a white light emitter.

To this end the third light source 106 may be a warm white light emitter and the third peak wavelength is within the range of 540-650 nm, see the dash-dotted line in FIG. 4. The illumination apparatus 100 may thereby provide an improved control of the color balance of the light emitted 112.

A warm white light emitter may be defied as a light source producing white light having a color temperature of 1600-4000 K CCT. To this end, A light source may be a neutral white light emitter which may be defied as a light source producing white light having a color temperature of 3700 to 5500 K CCT.

As a non-limiting example, the second light source may have a 50% intensity over a spectral wavelength range of at least 70 nm.

The skilled person realizes that the illumination apparatus may comprise a light source emitting substantially at a single wavelength. The light may be emitted around a single wavelength with a narrow spectral range having a full-width-at-half-maximum, FWHM, of about 4-10% of the central emission wavelength.

In the above discussion, the illumination apparatus 100, comprise light emitting diodes emitting light at a narrow wavelength range, cold light emitters and/or warm light emitters.

Figure 5:
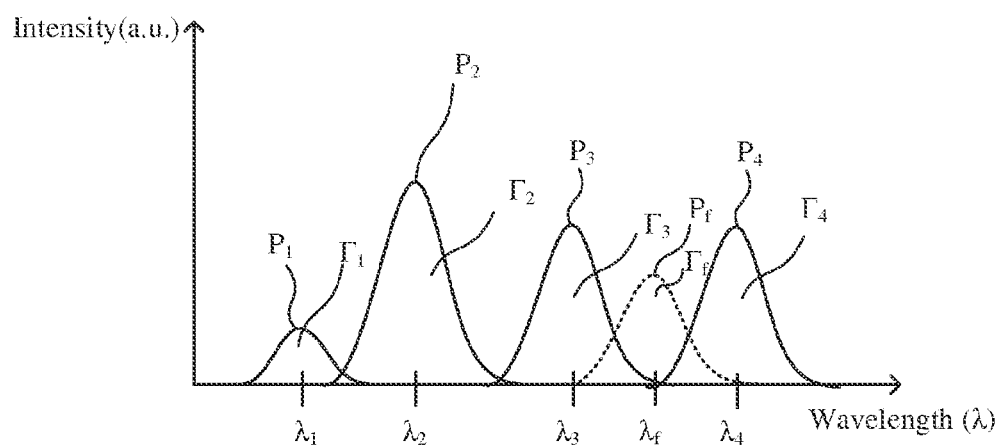
FIG. 5 illustrates a spectral distribution of light emitted by an illumination apparatus.

The illumination apparatus 100, may comprise at least three narrow band light emitters, such as light emitting diodes, as illustrated in FIG. 5. narrow band light emitters are configured to emit light around a predetermined central wavelength. The illumination apparatus 100 may be referred to as a red-green-blue light emitter, RGB-emitter. More specifically, the first 102 and second 104 light sources may be configured to emit light in the blue spectral range of the visible range. As a non-limiting example, the first light source 102 may be configured to emit light having a first spectral light distribution $\Gamma_1$ having a first main light intensity peak $P_1$ about a first peak wavelength $\lambda_1$ within the range of 450-490 nm which provides light stimulation as discussed above. The second light source 104 may be configured to emit light having a second spectral light distribution $\Gamma_2$ having a second main light intensity peak $P_2$ about a second peak wavelength $\lambda_2$ within the range of 440-450 nm or 490-500 nm. The first 102 and the second 104 light sources may therefore be referred to as a first, $B_1$, and a second $B_2$ blue light emitter, respectively. The third light source 106 may further be a green light emitter, G, configured to emit light having a third spectral light distribution $\Gamma_3$ having a third main light intensity peak $P_3$ about a third peak wavelength $\lambda_3$ within the range of 490-580 nm.

The third light source 106 may be a green light emitter, G, configured to emit light having a third spectral light distribution $\Gamma_3$ having a third main light intensity peak $P_3$ about a third peak wavelength $\lambda_3$ within the range of 520-560 nm.

It may be noted that, alternatively, third light source may be a red light emitter, R, and the third peak wavelength is within the range of 630-700 nm.

The third peak wavelength may be within the range of 640-700 nm.

The illumination apparatus 100 may further comprise a fourth light source, not shown, configured to emit light having a fourth spectral light distribution $\Gamma_4$ having a fourth main light intensity a $P_4$ about a fourth peak wavelength $\lambda_4$. The fourth peak wavelength is different from the first peak wavelength, from the second peak wavelength and from the third peak wavelength. The fourth light source may be a red light emitter, R, and the fourth peak wavelength is within the range of 630-700 nm, see FIG. 5.

The fourth peak wavelength may be within the range of 640-700 nm.

The illumination apparatus 100 is further configured to provide adjustment of light intensity of the fourth light source in to order to in combination with the adjusting of the third light source 106 compensate for the adjusting of the relative light intensity between the first light source 102 and the second light source 104.

The illumination apparatus 100 may thereby provide light emission over different color ranges of the visible spectrum. The colors of the light emitted may, moreover be mixed providing white light. The light emitted by the illumination apparatus may thereby have a more or a less stimulating effect by the relative intensity of the light emitted by the first 102 and the second 104 light sources.

The illumination apparatus 100 may further comprise a further light source, not shown, configured to emit light having a further spectral light distribution $\Gamma_f$ having a further main light intensity peak $P_f$ about a further peak wavelength $\lambda_f$, see the dashed line in FIG. 5. The further peak wavelength $\lambda_f$ is different from the first peak wavelength $\lambda_1$ and from the second peak wavelength $\lambda_2$. The illumination apparatus 100 may further be configured to provide adjustment of light intensity of the further light source. The further peak wavelength $\lambda_f$ may be chosen to enhance the light stimulation provided by the first light source 102.

As a non-limiting example, the further light may have a main light intensity peak $P_f$ at a peak wavelength within the range of 580-630 nm. Thus, the further light source allows for light exposure at longer wavelength light, i.e. 580-630 nm in the orange-red part of the visible spectrum. Light within the range of 580-630 nm may trigger melanopsin chromophore regeneration and an increased subsequent intrinsic photosensitivity of intrinsically photosensitive retinal ganglion cells, ipRGCs. An improved suppression of melanin may thereby be obtained. An illumination apparatus 100 providing increased stimulation may thereby be provided.

It should be noted that the illumination apparatus 100 may be configured to at a first point in time emit light from the further light source and from at a second point in time emit light from the first light source 102. A prior exposure to longer wavelength light, here exemplified by the orange light emitted by the further light source, relative to the shorter wavelength, exemplified by the blue light emitted by the first light source 102, enhances the subsequent impact of light on executive brain responses. An improved suppression of melatonin may thereby be obtained.

In the above the description it has been exemplified that the illumination apparatus illuminates a human. A skilled person, however, realizes that in other embodiments animals such as pets or livestock may be illuminated. The above mentioned benefits of the illumination apparatus for illuminating humans, when applicable, apply also to animals.

A method for controlling illumination may further be provided. The method comprising:

adjusting a relative light intensity between a first light source and a second light source, wherein the first light source is configured to emit light having a first spectral light distribution having a first main light intensity peak about a first peak wavelength providing light stimulation, and the second light source is configured to emit light having a second spectral light distribution having a second main light intensity peak about a second peak wavelength being different from the first peak wavelength, adjusting a light intensity of a third light source configured to emit light having a third spectral light distribution having a third main light intensity peak about a third peak wavelength being different from the first peak wavelength and from the second peak wavelength in to order to compensate for the adjusting of the relative light intensity between the first light source and the second light source.

The method according may further comprise adjusting a light intensity of a fourth light source configured to emit light having a fourth spectral light distribution having a fourth main light intensity about a fourth peak wavelength being different from the first peak wavelength, from the second peak wavelength and from the third peak wavelength in to order to in combination with the adjusting of the third light source compensate for the adjusting of the relative light intensity between the first light source and the second light source.

The adjusting of a light intensity may further comprise using a further light source configured to emit light having a further spectral light distribution having a further main light intensity peak about a further peak wavelength being different from the first peak wavelength and from the second peak wavelength, the further peak wavelength being chosen to enhance the light stimulation provided by the first light source.

The person skilled in the art realizes that the present invention by no means is limited to the preferred embodiments described above. On the contrary, many modifications and variations are possible within the scope of the appended claims.

For example, an illumination system may be provided. The illumination system comprising a first illumination apparatus and a second illumination apparatus, wherein the first illumination apparatus is configured to illuminate a first region in space, and the second illumination apparatus is configured to illuminate a second region in space, the first and the second regions being different. The above mentioned features of respective illumination apparatus have been described above. Thus, in order to avoid undue repetition, reference is made to the above. An advantage of the illumination system is that the relative light intensity between the first light source and the second light source for the first illumination apparatus may be different to the relative light intensity between the first light source and the second light source for the second illumination apparatus. The stimulation by light may thereby differ between in the first and the second regions. As respective first and the second illumination apparatus is further configured to provide adjustment of light intensity of the third light source to compensate for the adjusting of the relative light intensity the illumination system thereby allows for a tuning of the relative light intensity between the two regions while keeping a substantially unchanged spectral light distribution of the light emitted by the first and the second illumination apparatus. A more uniform illumination in a space may therefore be achieved while allowing for different regions in space having different degrees of stimulation. The first region may, for example, be stimulating while the second region is non-stimulating or at least less stimulating.

The first and the second regions may be partially overlapping. The first and the second regions may be physically separated, i.e. non-overlapping.

It may be noted that the stimulation effect is often referred to as related to blue light. However, the wavelength discussed above may according to some references be considered as green light. For sake of clarity, we have referred to blue light even if the wavelength intervals may comprise blue-green or even green light.

Additionally, variations to the disclosed embodiments can be understood and effected by the skilled person in practicing the claimed invention, from a study of the drawings, the disclosure, and the appended claims.

What is claimed is:

1. An illumination apparatus configured to induce a biological and/or behavioral effect on a human or animal, the illumination apparatus comprising:

a first light source configured to emit light having a first spectral light distribution having a first main light intensity peak about a first peak wavelength providing light stimulation, wherein the first peak wavelength is within the range of 470-490 nm, a second light source configured to emit light having a second spectral light distribution having a second main light intensity peak about a second peak wavelength being different from the first peak wavelength, wherein the second peak wavelength is shifted with at least ±7 nm as compared with the first peak wavelength and wherein the second peak wavelength is within 10% of the visible spectral wavelength range from the first peak wavelength;

a third light source configured to emit light having a third spectral light distribution having a third main light intensity peak about a third peak wavelength being different from the first peak wavelength and from the second peak wavelength, wherein the third peak wavelength is within the range of 500-700 nm; and a further light source configured to emit light having a further spectral light distribution having a further main light intensity peak about a further peak wavelength being different from the first peak wavelength and from the second peak wavelength, the further peak wavelength being chosen to enhance the light stimulation provided by the first light source, the further light has a main light intensity peak at a peak wavelength within the range of 580-630 nm, wherein the illumination apparatus is configured to provide relative adjustment of light intensity of the first light source and of light intensity of the second light source, thereby providing a relative light intensity between the first light source and the second light source, and wherein when the relative light intensity between the first light source and the second light source is adjusted, light intensity of the third light source is adjusted together with the adjustment of the relative light intensity between the first light source and the second light source in order to compensate change of the relative intensity between the first light source and the second light source, and light intensity of the further light source is adjusted together with the adjustment of the relative light intensity between the first light source and the second light source in order to enhance the light stimulation of the first light source which is changed by the relative intensity between the first light source and the second light source.

2. The illumination apparatus according to claim 1, wherein the second light source has a 50% intensity over a spectral wavelength range of at least 70 nm.

3. The illumination apparatus according to claim 1, wherein the third light source is a green light emitter and the third peak wavelength is within the range of 500-580 nm.

4. The illumination apparatus according to claim 1, wherein the third light source is a red light emitter and the third peak wavelength is within the range of 630-700 nm.

5. The illumination apparatus according to claim 1, further comprising a fourth light source configured to emit light having a fourth spectral light distribution having a fourth main light intensity about a fourth peak wavelength being different from the first peak wavelength, from the second peak wavelength and from the third peak wavelength, wherein the illumination apparatus is configured to provide adjustment of light intensity of the fourth light source in to order to in combination with the adjusting of the third light source compensate for the adjusting of the relative light intensity between the first light source and the second light source.

6. The illumination apparatus according to claim 5, wherein the fourth light source is a red light emitter and the fourth peak wavelength is within the range of 630-700 nm.

7. The illumination apparatus according to claim 1, wherein the illumination apparatus is configured to emit light from the further light source at a first point in time and from the first light source at a second point in time, the first point in time being prior to the second point in time.

8. The illumination apparatus according to claim 1, wherein adjustment of light intensity of the first light source and of light intensity of the second light source are made such that cortisol and/or melatonin levels in humans or animals exposed to light from the illumination apparatus is influenced.

9. The illumination apparatus according to claim 1, wherein the first light source is a cold white light emitter, wherein the second light source is a cold white light emitter and wherein the third light source is a warm white light emitter.

10. A light source assembly comprising:

a first light source configured to emit light having a first spectral light distribution having a first main light intensity peak about a first peak wavelength providing light stimulation, wherein the first peak wavelength is within the range of 470-490 nm;

a second light source configured to emit light having a second spectral light distribution having a second main light intensity peak about a second peak wavelength being different from the first peak wavelength, wherein the second peak wavelength is shifted with at least ±7 nm as compared with the first peak wavelength and wherein the second peak wavelength is within 10% of the visible spectral wavelength range from the first peak wavelength;

a third light source configured to emit light having a third spectral light distribution having a third main light intensity peak about a third peak wavelength being different from the first peak wavelength and from the second peak wavelength, wherein the third peak wavelength is within the range of 500-580 nm;

a fourth light source configured to emit light having a fourth spectral light distribution having a fourth main light intensity about a fourth peak wavelength being different from the first peak wavelength, from the second peak wavelength and from the third peak wavelength, wherein the fourth light source is a red light emitter and the fourth peak wavelength is within the range of 630-700 nm; and a further light source configured to emit light having a further spectral light distribution having a further main light intensity peak about a further peak wavelength being different from the first peak wavelength and from the second peak wavelength, the further peak wavelength being chosen to enhance the light stimulation provided by the first light source, the further light has a main light intensity peak at a peak wavelength within the range of 580-630 nm.

11. The light source assembly according to claim 10, wherein the first light source is a cold white light emitter, wherein the second light source is a cold white light emitter and wherein the third light source is a warm white light emitter.

* * * * *